United States Patent

Archer et al.

[11] 3,974,230
[45] Aug. 10, 1976

[54] STABILIZED 1,1,1-TRICHLOROETHANE
[75] Inventors: Wesley L. Archer; David R. Spencer, both of Midland, Mich.
[73] Assignee: The Dow Chemical Company, Midland, Mich.
[22] Filed: Dec. 9, 1974
[21] Appl. No.: 530,588

[52] U.S. Cl. .................................... 260/652.5 R
[51] Int. Cl.² ........................................ C07C 17/40
[58] Field of Search ............................ 260/652.5 R

[56] References Cited
UNITED STATES PATENTS

| | | | |
|---|---|---|---|
| 3,281,480 | 10/1966 | Hardies | 260/652.5 R |
| 3,326,989 | 6/1967 | Cormany et al. | 260/652.5 R |
| 3,549,715 | 12/1970 | Cormany et al. | 260/652.5 R |

Primary Examiner—D. Horwitz
Attorney, Agent, or Firm—Glwynn R. Baker

[57] ABSTRACT 1,1,1-trichloroethane containing as the essential metal stabilizers (1) from 3.5 to 6 volume percent of (a) a mixture of 3-methyl-1-butyn-3-ol

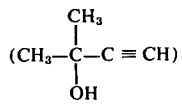

and tertiary amyl alcohol

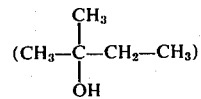

wherein said 3-methyl-1-butyn-3-ol is present in at least 1.75 volume percent of said mixture or (b) 3.5 volume percent 3-methyl-1-butyn-3-ol; (2) 0.5 to 2 volume percent of a nitroalkane selected from nitromethane or a mixture of nitromethane and nitroethane, said nitromethane or mixture of nitroalkanes being present in at least 1.0 volume percent when said mixture (1a) is 3.5 volume percent and 0.75 volume percent when said (1b) is 3.5 volume percent; and, (3) 0.5 to 1 volume percent of an alkylene oxide having 4 to 6 carbon atoms including cyclohexene oxide as the essential acid acceptor. A preferred composition consists of 2 volume percent each of 3-methyl-1-butyn-3-ol and tertiary amyl alcohol, 1.0 volume percent nitromethane and 0.75 volume percent 1,2-butylene oxide.

3 Claims, No Drawings

STABILIZED 1,1,1-TRICHLOROETHANE

BACKGROUND OF INVENTION

Numerous patents have issued disclosing organic compounds as stabilizers for 1,1,1-trichloroethane. One of the earliest patents granted, U.S. Pat. No. 2,838,811, disclosed that 1,4-dioxane (the cyclic diether derived from diethylene glycol) alone or in combination with a nonprimary acetylenic alcohol was useful to stabilize 1,1,1-trichloroethane. Previously, secondary and tertiary butyl alcohols have been added as storage stabilizers. These butanol-stabilized compositions have limited effectiveness in cold cleaning of aluminum and its alloys but seem suitable for iron, and its alloys. With the increased demand for this unique solvent because of its relative safety, i.e., no Tag Open Cup flash point and high threshold limit value (TLV), into, for example, hot cleaning, i.e., dipping metal parts into warm or hot (boiling) 1,1,1-trichloroethane, research efforts to find a suitable stabilizer for 1,1,1-trichloroethane-white metal reaction resulted in the discovery of 1,4-dioxane. Since this first patent, directed specifically to solving 1,1,1-trichloroethane's unique problem of reactivity toward white metals (aluminum and zinc), some 90 to 100 patents have issued to inventors in the United States alone. These patents disclose literally hundreds of organic compounds as suitable for stabilizing 1,1,1-trichloroethane in the presence of metals, particularly aluminum. However, of these hundreds of compounds only a few, less than 10 in number, have found commercial acceptability in the marketplace principally because outside of these 10, the remainder require impractically high concentrations, or are expensive, or are in short supply, and/or perform unacceptably under the general use conditions found in industry. A few, again less than 10, have found limited commercial acceptability in special areas such as aerosols, film cleaning and the like, where careful control by the user is taken to avoid contact with aluminum.

Since the introduction into the marketplace in 1957–1958 as a commodity the largest volume of 1,1,1-trichloroethane sold throughout the world contained, and still contains, 1,4-dioxane, nitromethane and 1,2-butylene oxide as the sole inhibitors. The next largest volume has been that containing 1,3-dioxolane (a five-membered dioxygen heterocycle, a compound very similar to 1,4-dioxane), nitromethane, 1,2-butylene oxide and in most instances one or more materials (such as lower ketones and/or alcohols which accounts for the remainder of the ten principal compounds used in industry to stabilize 1,1,1-trichloroethane).

Aerosol and film cleaning uses do not require stabilization to the same type as metal cleaning applications which latter subject the 1,1,1-trichloroethane to the most severe physical and chemical stresses. Therefore, in aerosol applications, not only is less stabilizer present but less effective stabilizers can be employed. Most stabilizers for 1,1,1-trichloroethane aerosol usage are ones which do not create odor problems when mixed with the components of aerosol formulations. Film cleaning 1,1,1-trichloroethane compositions contain stabilizers which do not dissolve the emulsions from photographic film. Many of the 1,1,1-trichloroethane solvents sold into the aerosol market contain methylal (dimethoxymethane), am alkylene oxide, e.g., propylene oxide, and an alcohol, e.g., secondary or tertiary butyl alcohol.

In the light of recent attacks by environmentalists on some of the chlorinated hydrocarbons allegedly due to their environmental hazards as well as controls concerning their use resulting from the recently enacted Occupational Safety and Health Act, it becomes necessary for the manufacturers of 1,1,1-trichloroethane to provide this safer solvent, from an environmental, safety and health standpoint, with inhibitor systems which will be in conference with environmental standards.

It is the object of the present invention to provide an industrially useful combination of stabilizers for 1,1,1-trichloroethane which will inhibit, even under the severe stress of vapor degreasing, the 1,1,1-trichloroethane-aluminum reaction as well as the reactions attributable to the presence of zinc, copper and iron, their alloys, and water.

These and other objects will become apparent to those skilled in the art from the following description and claims.

BRIEF DESCRIPTION OF INVENTION 1,1,1-trichloroethane containing as the essential metal stabilizers (1) from 3.5 to 6 volume percent of (a) a mixture of 3-methyl-1-butyn-3-ol

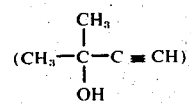

and t. amyl alcohol

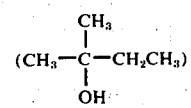

wherein said 3-methyl-1-butyn-3-ol is present in at least 1.75 volume percent of said mixture or (b) 3.5 volume percent 3-methyl-1-butyn-3-ol; (2) 0.5 to 2 vol. percent of a nitroalkane selected from nitromethane or a mixture of nitromethane and nitroethane, said nitromethane or mixture of nitroalkanes being present in at least 1.0 volume percent when said mixture (1a) is 3.5 volume percent and 0.75 volume percent when said (1b) is 3.5 volume percent; and, (3) 0.5 to 1 volume percent of an alkylene oxide having 4 to 6 carbon atoms including cyclohexane oxide as the essential acid acceptor. Good results have been achieved in industrial metal cleaning applications when at least 2 volume percent each of tertiary amyl alcohol and 3-methyl-1-butyn-3-ol, 0.75 volume percent 1,2-butylene oxide and 1.0 volume percent nitromethane have been incorporated in 1,1,1-trichloroethane.

DETAILED DESCRIPTION OF INVENTION

The principal inhibitors, tertiary amyl alcohol and 3-methyl-1-butyn-3-ol, are not effective stabilizers under severe stress alone and must be used in the presence of the nitroalkanes and/or epoxides. The following tables set forth the results of several tests made to determine the effectiveness of the principal inhibitors and their coadditives.

To demonstrate an inhibitor's effectiveness alone to stabilize against 1100 Al (99$^+$% Al), the easiest of the aluminums to stabilize, hot scratch tests were conducted as follows:

Procedure

Fifty cc of the 1,1,1-trichloroethane formulation (the 1,1,1-trichloroethane used for all the following tests contains 500 ppm 1,2-butylene oxide) is placed in a Pyrex petri dish (9 cm diameter by 2½ cm deep) and placed on a hot plate. The solvent is allowed to heat to just below a rolling boil and then taken off the hot plate. A 2½ inch × ½ inch × ⅛ inch thick 1100 Al coupon is immediately placed in the petri dish and the surface of the coupon is scratched (three times lengthwise and three times crosswise at right angles to and through the lengthwise scratches) with a stylus while the coupon is submerged.

The petri dish is then covered and is observed at room temperature for one hour. After one hour a "scratch rating" is given to the appearance of the scratch sites:

| Scratch Rating | Description |
| --- | --- |
| 0 | Scratches are completely inhibited with no reaction products. |
| 1 | Scratches immediately cure with isolated sites of reaction product. |
| 2 | Scratches rapidly cure but with some formation of reaction products. |
| 3 | Scratches slowly cure but with much formation of reaction products. |
| 4 | Little inhibition at scratch sites with a slow continuing reaction. |
| 5 | "Run away" reaction — Before the 1 hour observation period the solution turns black, HCl is generated, a fast ongoing reaction is present at scratch sites. |

After the coupon is rated, the solution is filtered through an Eaton Dikeman No. 509 round fluted filter paper and collected for color rating. Color ratings are done with a Hallige Lab Comparator using a 5 to 100 yellow color disk. The solutions were compared to water using 50 cc Nessler tubes. Color rating is from 5 to 70 APHA number (American Public Health Association). When the APHA value was greater than 70 the solution was diluted with a known volume of 1,1,1-trichloroethane and the APHA value determined by a linear relationship between dilution factor and APHA number.

The following abbreviations will be used in the tables:
MBy = 3-methyl-1-butyn-3-ol
TAA = tertiary amyl alcohol
NM = nitromethane
NE = nitroethane
BO = 1,2-butylene oxide Table I Hot 1100 Aluminum Scratch Tests with MBy; TAA; NM; BO and Mixtures as Inhibitors for 1,1,1-Trichloroethane

| Ex. No. | Volume % Inhibitor | | | | Scratch Rating | APHA Color |
| --- | --- | --- | --- | --- | --- | --- |
| | MBy | TAA | NM | BO | | |
| 1 | 3 | — | — | — | 4 | 1250 |
| 2 | 4 | — | — | — | 3 | 750 |
| 3 | 5 | — | — | — | 2 | 50 |
| 4 | 6 | — | — | — | 1 – 2 | 50 |
| 5 | 7 | — | — | — | 2 | 80 |
| 6 | 8 | — | — | — | 0 | 20 |
| 7 | — | 4 | — | — | 4 | 2000 |
| 8 | — | 5 | — | — | 1 | 50 |
| 9 | — | 6 | — | — | 0 | <10 |
| 10 | — | 7 | — | — | 0 | <10 |
| 11 | — | — | 2 | — | 5(1m)* | |
| 12 | — | — | 3 | — | 5 | |
| 13 | — | — | 3 ½ | — | 3 – 4 | 3000 |
| 14 | — | — | 4 | — | 2 | 750 |
| 15 | — | — | 5 | — | 0 | <10 |
| 16 | — | — | 6 | — | 0 | <10 |
| 17 | — | — | — | 4 | 5(5m) | |
| 18 | — | — | — | 5 | 5(5m) | |
| 19 | — | — | — | 7 | 5(15m) | |
| 20 | — | — | — | 8 | 5(15m) | |
| 21 | — | — | — | 9 | 3 | >8000 |
| 22 | — | — | — | 10 | 2 | 2000 |

*The parentheses indicate the approximate starting time, in minutes (m), of the "runaway" reaction.

The above compounds were then mixed in various proportions to determine their joint effect. The test procedure was the same. The results are reported below:

Table II

Hot 1100 Aluminum Stratch Tests with MBy; TAA, NM; BO and Mixtures as Inhibitors for 1,1,1-Trichloroethane

| Ex. No. | Volume % Inhibitor | | | | Scratch Rating | APHA Color |
| --- | --- | --- | --- | --- | --- | --- |
| | MBy | TAA | NM | BO | | |
| 23 | 3 | 1 | — | — | 1 | 50 |
| 24 | 2 | 2 | — | — | 1 | 80 |
| 25 | 1 | 3 | — | — | 2 | 500 |
| 26 | 3 | — | 1 | — | 0 | 20 |
| 27 | 2 | — | 2 | — | 0 | 20 |
| 28 | 1 | — | 3 | — | 0–1 | 20 |
| 29 | — | 3 | 1 | — | 0–1 | 20 |
| 30 | — | 2 | 2 | — | 0 | 20 |
| 31 | — | 1 | 3 | — | 4 | 4000 |
| 32 | 2 | 1 | 1 | — | 0 | <10 |
| 33 | 1.33 | 1.33 | 1.33 | — | 0 | |
| 34 | 1 | 2 | 1 | — | 0 | |
| 35 | 1 | 1 | 2 | — | 0 | |
| 36 | 3 | — | — | 1 | 4 | >8000 |
| 37 | 2 | — | — | 2 | 5(5m) | |
| 38 | 1 | — | — | 3 | 5(5m) | |
| 39 | — | 3 | — | 1 | 5(15m) | |
| 40 | — | 2 | — | 2 | 5(5m) | |
| 41 | — | 1 | — | 3 | 5(5m) | |
| 42 | — | — | 3 | 1 | 2 | 500 |
| 43 | — | — | 2 | 2 | 3 | 2000 |
| 44 | — | — | 1 | 3 | 5 | |
| 45 | 2 | 1 | — | 1 | 4 | >8000 |
| 46 | 1 | 2 | — | 1 | 4 | >8000 |
| 47 | 2 | — | 1 | 1 | 1 | 350 |
| 48 | 1 | — | 2 | 1 | 2 | 1250 |
| 49 | — | 2 | 1 | 1 | 2 | 1250 |
| 50 | — | 1 | 2 | 1 | 0/2 | 50/1250 |
| 51 | 1 | 1 | 1 | 1 | 1 | 350 |
| 52 | 2 | 1 | 0.5 | 0.5 | 0 | 20 |
| 53 | 1 | 2 | 0.5 | 0.5 | 0 | 20 |
| 54 | — | 2 | 1 | 0.5 | 0 | 50 |
| 55 | 1 | 1 | 1 | 0.5 | 0 | 50 |
| 56 | 2 | — | 1 | 0.5 | 0 | 80 |
| 57 | — | 2 | 0.5 | 0.5 | 4 | >8000 |

Aluminum Hot Scratch Test

In conjunction with the hot scratch tests above run with 1100 aluminum coupons (99.0$^+$% Al), a series of hot scratch tests was also run with 2024 aluminum coupons (93.4% Al, 4.5% Cu, 1.5% Mg, 0.6% Mn) in various inhibited 1,1,1-trichloroethane formulations. 2024 Al was tested since past experience indicates that the Al/Cu alloy (commonly encountered in metals which are subjected to vapor degreasing) poses a more difficult stabilization problem than does pure (1100) aluminum.

The same test procedure was followed as described for the 1100 Al test series except that three lengthwise scratches and five crosswise scratches were inscribed on the 2024 Al coupons. Following are the tabulated results:

Table III

| MBy | Volume % Inhibitor TAA | NM | BO | Hot Scratch Rating | APHA Color |
|---|---|---|---|---|---|
| 6 | | | | 2 | 80 |
| 5 | | | | 3 | 350 |
| 4 | | | | 4 | 2000 |
| 3 | | | | 4 | 1500 |
| | 6 | | | 4 | 500 |
| | 5 | | | 4 | 1250 |
| | 4 | | | 4 | 1250 |
| | 3 | | | 5 (50 min) | — |
| | | 8 | | 0 | <10 |
| | | 7 | | 0 | <10 |
| | | 6 | | 2 | 200 |
| | | 5.5 | | 3 | 950 |
| | | 5 | | 5 (30 min) | — |
| | | | 9 | 3 | 1500 |
| | | | 8 | 3 | 2500 |
| | | | 7 | 4 | 6000 |
| | | | 6 | 4 | >8000 |
| | | | 5 | 5 (45 min) | — |
| 4.5 | 1.5 | | | 3 | 70 |
| .3 | 3 | | | 3 | 60 |
| 1.5 | 4.5 | | | 4 | 300 |
| 3.75 | 1.25 | | | 2 | 50 |
| 2.5 | 2.5 | | | 3 | 250 |
| 1.25 | 3.75 | | | 4 | 450 |
| 3 | 1 | | | 3 | 750 |
| 2 | 2 | | | 4 | 1750 |
| 1 | 3 | | | 4 | 1750 |
| 2.25 | .75 | | | 4 | 5000 |
| 1.5 | 1.5 | | | 4 | 2500 |
| .75 | 2.25 | | | 5 (40 min) | — |
| 5.5 | | 0.5 | | 0 | <10 |
| 4.5 | | 0.5 | | 1 | 30 |
| 3.5 | | 0.5 | | 2 | 300 |
| 2.5 | | 0.5 | | 4 | 2250 |
| | 5.5 | 0.5 | | 1 | 80 |
| | 4.5 | 0.5 | | 4 | 1875 |
| | 3.5 | 0.5 | | 5 (50 min) | — |
| | 2.5 | 0.5 | | 5 (10 min) | — |
| 5 | | 1 | | 1 | <10 |
| 4 | | 1 | | 2 | 50 |
| 3 | | 1 | | 2 | 100 |
| 2 | | 1 | | 5 (15 min) | — |
| | 5 | 1 | | 3 | 250 |
| | 4 | 1 | | 4 | 2000 |
| | 3 | 1 | | 4 | 3000 |
| 4.5 | | 1.5 | | 0 | <10 |
| 3.5 | | 1.5 | | 1 | 30 |
| 2.5 | | 1.5 | | 4 | 2200 |
| | 4.5 | 1.5 | | 1 | 30 |
| | 3.5 | 1.5 | | 3 | 250 |
| | 2.5 | 1.5 | | 4 | 1750 |
| 4.12 | 1.38 | 0.5 | | 0 | <10 |
| 2.75 | 2.75 | 0.5 | | 0 | <10 |
| 1.38 | 4.12 | 0.5 | | 1 | 30 |
| 3.37 | 1.13 | 0.5 | | 2 | 125 |
| 2.25 | 2.25 | 0.5 | | 2 | 300 |
| 1.13 | 3.37 | 0.5 | | 3 | 500 |
| 2.62 | .88 | 0.5 | | 4 | 875 |
| 1.75 | 1.75 | 0.5 | | 4 | 2000 |
| .88 | 2.62 | 0.5 | | 4 | 3000 |
| 1.87 | .63 | 0.5 | | 4 | 4000 |
| 1.25 | 1.25 | 0.5 | | 5 (25 min) | — |
| .63 | 1.87 | 0.5 | | 5 (15 min) | — |
| 3.75 | 1.25 | 1 | | 1 | 15 |
| 2.5 | 2.5 | 1 | | 1 | 20 |
| 1.25 | 3.75 | 1 | | 2 | 100 |
| 3 | 1 | 1 | | 2 | 60 |
| 2 | 2 | 1 | | 4 | 400 |
| 1 | 3 | 1 | | 4 | 450 |
| 2.25 | .75 | 1 | | 4 | 2750 |
| 1.5 | 1.5 | 1 | | 5 (55 min) | — |
| .75 | 2.25 | 1 | | 5 (45 min) | — |
| 3.4 | 1.1 | 1.5 | | 0 | <10 |
| 2.25 | 2.25 | 1.5 | | 0 | 10 |
| 1.1 | 3.4 | 1.5 | | 1 | 20 |
| 2.6 | .9 | 1.5 | | 1 | 30 |
| 1.75 | 1.75 | 1.5 | | 1 | 40 |
| .9 | 2.6 | 1.5 | | 2 | 50 |
| 1.9 | .6 | 1.5 | | 4 | 1500 |
| 1.25 | 1.25 | 1.5 | | 4 | 2300 |
| .6 | 1.9 | 1.5 | | 4 | 1500 |
| | | 4.5 | 1.5 | 0 | <10 |
| 3 | 3 | 0 | | <10 | |
| 1.5 | 4.5 | 0 | | <10 | |
| 3.75 | 1.25 | 2 | | 1400 | |
| 2.5 | 2.5 | 2 | | 1600 | |
| 1.25 | 3.75 | 1 | | 350 | |
| 3 | 1 | | | 5 (3 min) | — |
| 2 | 2 | | | 5 (25 min) | — |
| 1 | 3 | | | 5 (10 min) | — |
| 5 | — | | | 3 | 1500 |
| 3.75 | 1.25 | | | 3 | 875 |
| 2.5 | 2.5 | | | 3 | 1000 |
| 1.25 | 3.75 | | | 5 (45 min) | — |
| — | 5 | | | 4 | 7000 |
| 4.5 | — | 1 | .5 | 0 | <10 |
| 3.4 | 1.1 | 1 | .5 | 0 | <10 |
| 2.25 | 2.25 | 1 | .5 | 1 | 175 |
| 1.1 | 3.4 | 1 | .5 | 1 | 200 |
| — | 4.5 | 1 | .5 | 4 | 950 |
| 3.5 | — | 1 | .5 | 1 | 200 |
| 2.6 | .9 | 1 | .5 | 2 | 850 |
| 1.75 | 1.75 | 1 | .5 | 4 | 2500 |
| .9 | 2.6 | 1 | .5 | 4 | 2000 |
| — | 3.5 | 1 | .5 | 4 | 7000 |

| MBy | TAA | NM/NE | BO | Hot Scratch Rating | APHA |
|---|---|---|---|---|---|
| 1 | — | 2/— | .05 | 5 (3 min) | — |
| 2 | — | 2/— | .05 | 5 (8 min) | — |
| 3 | — | 2/— | .05 | 1 | 30 |
| 2 | — | 1.25/0.-375 | .05 | 5 (20 min) | — |
| 2 | — | .75/.75 | .05 | 5 (15 min) | — |
| 2 | — | .375/1.-125 | .05 | 5 (12 min) | — |

General conclusions can be drawn from the data presented in Tables I, II and III. The "hot" scratch tests simulate stresses that may be present in hot cleaning and vapor degreasing environments that expose hot 1,1,1-trichloroethane to aluminum metal. Inhibitors, or combinations of inhibitors, that, at specified concentration levels, give "0" or "1" hot stratch ratings, are considered as adequate inhibitors of the 1,1,1-trichloroethane-aluminum reaction in hot solvent environments, while "3", "4" and "5" ratings are considered as unacceptable. A "2" rating is borderline and is an indication of the lower limit of effective inhibitor concentration. Applying these factors, the following generalizations can be made based on 1100 and 2024 aluminum hot scratch data presented previously:

1. Mixtures of MBy and TAA better than equal concentrations of either MBy or TAA alone.

2. Mixtures of MBy and NM or TAA and NM are likewise more effective than either MBy or TAA or NM alone at equal concentrations.

3. Addition of NM to mixtures of MBy and TAA gives improved stabilization.

4. Substitution of BO for NM in MBy and TAA mixtures yields inferior stabilization. NOTE: While 1,2-butylene oxide does not contribute to stabilization of the 1,1,1-trichloroethane-aluminum reaction, the epoxide has proved, by past experience, to be invaluable to the overall stabilizer package due to its acid acceptance properties. Indeed, irrespective of the white metal-1,1,1-trichloroethane reaction, small amounts of hydrochloric acid are generated in a hot 1,1,1-trichloroethane environment. This acid, if not neutralized by an acid acceptor such as 1,2-butylene oxide, could cause corrosion of parts and equipment. Thus, a nominal amount of 1,2-butylene oxide, 0.5% to 1.0% (by volume) is needed in a 1,1,1-trichloroethane stabilizer package.

5. Finally, evaluating the data shown in Tables I, II and III, particularly the 2024 Al data which is the alloy of widest industrial contact, we can establish the minimum concentration:
   a. 1.75% MBy, 1.75% TAA, 1.0% NM (with 0.5 volume percent 1,2-butylene oxide as acid acceptor)
   if
      i. 1.75% MBy + 1.75% TAA + 1.0% NM + 0.5% BO gives a 2024 Al hot scratch rating of 4;
      ii. 2.25% MBy + 2.25% TAA + 1.0% NM + 0.5% BO gives a 2024 Al hot scratch rating of 1; and,
      iii. 1.0% MBy + 1.0% TAA + 1.0% NM + 0.5% BO gives a 1100 Al hot scratch rating of 0.
   Then, for industrial uses, a minimum safe concentration is at least 1.75% MBy and particularly greater than 1.75% MBy if the TAA is at 1.75% also.
   b. 3.5% MBy + 0.75% NM with 0.5 volume percent 1,2-butylene oxide
   if
      i. 2.5% MBy + 1.5% NM gives a 2024 Al hot scratch rating of 4;
      ii. 3% MBy + 1.0% NM gives a 2024 Al 2 rating;
      iii. 3.5% MBy + 1.0% NM + 0.5% BO gives a 2024 Al 1 rating; and,
      iv. 2% MBy + 1.0% NM + 0.5% BO gives a 1100 Al rating of 0.
   Then 3.5% MBy requires 0.75% NM.

To further demonstrate the necessity for nitroalkanes, the following test was run on various compositions including those of the present invention employing 1,1,1-trichloroethane:

Procedure

1. Distill the formulated mixture into three equal fractions.
2. To 100 g of each fraction add 100 g toluene, 18 g (1100) flakes, 0.7 g aluminum chloride and reflux same for 18 hours.
3. A reaction (noted by the solution turning black) occurring during the 18 hour test period constitutes a failure (F), while no reaction during the test period passes (P) the formulation.

This test is an attempt to initiate a Friedel-Crafts reaction, and measures the success of a stabilizer system in inhibiting that reaction.

Table IV

| MBy | TAA | NM/NE | Result |
|---|---|---|---|
| 2 | — | 2/— | P |
| 1 | — | 2/— | P |
| 0.5 | — | 2/— | F |
| 3 | — | 2/— | P |
| 3 | — | 1/— | F |
| 2 | — | 1.5/— | P |
| 1 | — | 1.5/— | F |
| 2 | — | 1/— | F |
| — | 3 | 1.5/— | F |
| .3 | — | 0.5/0.5 | F |
| 2 | — | 1/1 | P |
| 2 | — | .75/.75 | P |
| 2 | — | 1.125/0.375 | P |
| 2 | — | 0.375/1.125 | F |
| 1.5 | 1.5 | 1.5/— | P |
| 1.5 | 1.0 | 1.5/— | P |
| 1.5 | 0.5 | 1.5/— | P |
| 1.0 | 1.5 | 1.5/— | P |
| 1.0 | 1.0 | 1.5/— | P |
| 2 | 2 | 1.0/— | F |

The failures, when failure occurred, were always noted in the third fraction which always contained the least nitromethane. The three fractions would have stabilizer present according to the following table:

Table V

|  | NM | NE | BO | MBy | TAA |
|---|---|---|---|---|---|
| First fraction | 1.78 | 0.62 | 0.86 | 2.2 | 1.5 |
| Second fraction | 1.33 | 0.78 | 0.80 | 2.0 | 1.7 |
| Third fraction | 0.79 | 1.54 | 0.70 | 1.9 | 3.3 |
| Original concentration before distillation | 1.5 | 1.0 | 0.75 | 2.0 | 2.0 |

For other concentrations, proportionately larger or smaller amounts would be present in the fractions. The data suggests that those formulations which contain less than about 0.7 volume percent nitroalkane in any fraction fail. Thus, it is necessary to provide a formulation which will on partitioning contain at least 0.7 volume percent nitroalkane in each fraction. Note that a mixture of nitromethane and nitroethane inhibitor in a 1,1,1-trichloroethane formulation would provide a higher concentration of nitroalkanes in the third distillation fraction (i.e., the higher boiling sump of a vapor degreaser) because of the partitioning behavior of nitroethane noted in Table V. Of course, nitromethane alone is not capable of stabilizing under industrial usage as the earlier tests clearly demonstrate.

3-Methyl-1-butyn-3-ol is shown in the following test to give some protection under certain conditions to hydrolysis of the 1,1,1-trichloroethane as evidenced by the low percent loss of stabilizers, particularly 1,2-butylene oxide, which would be used up as a result of the acid generated during hydrolysis.

Wet Corrosion Test

Ninety cc of each formulation, 1 cc $H_2O$, and 5 gms each 2024 Al fines, 70/30 brass fines, mossy zinc, and iron filings are placed in a 250 cc stoppered flask. The flasks sit at room temperature and are shaken once a day.

Below are vapor phase chromatography determinations of inhibitor concentrations:

Table VI

|  | Before Test | % Lost (+ Indicates Gain) | | |
|---|---|---|---|---|
|  |  | 3 Days | 10 Days | 24 Days |
| % BO | 0.50 | 0 | +4 | 58 |
| % NM | 0.50 | 6 | 92 | 100 |
| % TAA | 3.0 | 0 | 0 | 0 |
| % BO | 0.50 | 0 | 2 | 0 |
| % NM | 0.50 | 0 | 2 | 8 |
| % MBy | 3.0 | 3 | 3 | 3 |

To compare the usefulness of the 3-methyl-1-butyn-3-ol to other inhibitors used today, the same test was run on tertiary butyl alcohol and 1,4-dioxane. Both lost 100% of the 1,2-butylene oxide in 24 days.

What is claimed is:

1. A composition of matter consisting essentially of 1,1,1-trichloroethane and an effective amount of stabilizers sufficient to stabilize said composition from reacting with metals, said effective amount of stabilizers being: (1) from 3.5 to 6 volume percent of component (a) a mixture of 3-methyl-1-butyn-3-ol having the formula

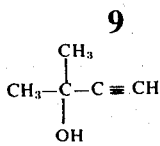

and t. amyl alcohol having the formula

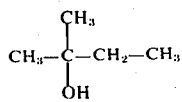

wherein said 3-methyl-1-butyn-3-ol is present in at least 1.75 volume percent of said mixture or component (b) 3.5 volume percent 3-methyl-1-butyn-3-ol; (2) 0.5 to 2 volume percent of a nitroalkane selected from nitromethane or a mixture of nitromethane and nitroethane, said nitromethane or mixture of nitroalkanes being present in at least 1.0 volume percent when said component (1a) is 3.5 volume percent and at least 0.75 volume percent when said component is (1b); and, (3) 0.5 to 1 volume percent of an alkylene oxide having 4 to 6 carbon atoms including cyclohexene oxide as the essential acid acceptor.

2. The composition of claim 1 wherein said 3-methyl-1-butyn-3-ol and said tertiary amyl alcohol are each present in 2 volume percent, said nitromethane is present in 1.0 volume percent and said 1,2-butylene oxide is present in 0.75 volume percent.

3. The composition of claim 1 wherein said nitroalkane is a mixture of nitromethane and nitroethane.

* * * * *

UNITED STATES PATENT AND TRADEMARK OFFICE
CERTIFICATE OF CORRECTION

PATENT NO. : 3,974,230
DATED : August 10, 1976
INVENTOR(S) : Wesley L. Archer; David R. Spencer It is certified that error appears in the above-identified patent and that said Letters Patent are hereby corrected as shown below:

Col. 1, line 12, delete "have" and insert -- had --

Col. 1, line 66, delete "am" and insert -- an --

Col. 2, line 9, delete "conference" and insert -- conformance --

Col. 2, line 52, delete "cyclohexane" and insert -- cyclohexene --

Col. 4, Table II, in first line of heading, delete "Stratch" and insert -- "Scratch --

Col. 6, line 36, delete "stratch" and insert -- scratch --

Col. 6, line 45, after "TAA" insert -- perform --

Col. 7, line 38, after "(1100)" insert -- aluminum --

Signed and Sealed this

Ninth Day of November 1976

[SEAL]

Attest:

RUTH C. MASON
Attesting Officer

C. MARSHALL DANN
Commissioner of Patents and Trademarks